US010283399B2

(12) United States Patent
Orvedahl (10) Patent No.: US 10,283,399 B2
(45) Date of Patent: *May 7, 2019

(54) SENSOR ARRAY WITH ANTI-DIFFUSION REGION(S) TO EXTEND SHELF LIFE

(71) Applicant: Siemens Healthcare Diagnostics Inc., Tarrytown, NY (US)

(72) Inventor: Donna S. Orvedahl, Medfield, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/984,751

(22) Filed: May 21, 2018

(65) Prior Publication Data

US 2018/0277419 A1  Sep. 27, 2018

Related U.S. Application Data

(63) Continuation of application No. 15/535,954, filed as application No. PCT/US2015/066363 on Dec. 17, 2015, now Pat. No. 9,978,633.

(Continued)

(51) Int. Cl.
*H01L 21/02* (2006.01)
*H01L 21/22* (2006.01)
(Continued)

(52) U.S. Cl.
CPC .......... *H01L 21/762* (2013.01); *G01N 27/27* (2013.01); *H01L 28/57* (2013.01);
(Continued)

(58) Field of Classification Search
CPC ....................................................... H01L 28/57
(Continued)

(56) References Cited

U.S. PATENT DOCUMENTS 5,585,069 A * 12/1996 Zanzucchi ........... B01J 19/0046
204/450
5,891,630 A    4/1999 Eggers et al.
(Continued)

FOREIGN PATENT DOCUMENTS

CN    102719352 A    10/2012

OTHER PUBLICATIONS

International Search Report and Written Opinion of International Application No. PCT/US2015/066363 dated Mar. 11, 2016.
(Continued)

*Primary Examiner* — Calvin Lee
(74) *Attorney, Agent, or Firm* — Kyle D. Petaja (57) ABSTRACT

The inventive concepts disclosed herein are generally directed to a sensor array device that has a prolonged shelf life but requires only a minimal amount of sample volume in order to test two or more analytes concurrently. In order to ensure the sensor array has a sufficient shelf life, anti-diffusion regions are positioned among the reaction wells in order to slow the processes of diffusion. The use of anti-diffusion regions, as described herein, can be used to optimize the number of sensors that can be fit into a sensor array designed for reduced sample liquid volumes (e.g., less than 100 μL) as well as extending the test strip's shelf life.

18 Claims, 3 Drawing Sheets

Related U.S. Application Data (60) Provisional application No. 62/094,478, filed on Dec. 19, 2014.

(51) Int. Cl.
    *H01L 21/762*  (2006.01)
    *G01N 27/27*   (2006.01)
    *H01L 49/02*   (2006.01)

(52) U.S. Cl.
    CPC ............ *B01J 2219/00317* (2013.01); *B01J 2219/00644* (2013.01); *B01J 2219/00653* (2013.01)

(58) Field of Classification Search
    USPC ................................ 438/551–556; 257/486
    See application file for complete search history.

(56) References Cited

U.S. PATENT DOCUMENTS

| | | |
|---|---|---|
| 7,074,700 B2 | 7/2006 | Huang |
| 9,978,633 B2 * | 5/2018 | Orvedahl .............. H01L 21/762 |
| | | 257/486 |
| 2005/0064678 A1 | 3/2005 | Dudek et al. |
| 2006/0216203 A1 | 9/2006 | Fuller et al. |
| 2008/0277764 A1 | 11/2008 | Ferru |
| 2012/0261264 A1 | 10/2012 | Srinivasan et al. |
| 2013/0023039 A1 | 1/2013 | Zaccarin et al. |

OTHER PUBLICATIONS

European Search Report and Written Opinion of European Application No. 15871063.2 dated Oct. 27, 2017.

Liu et al., "Development of microplate-based photoelectrochemical DNA biosensor array for high throughput detection of DNA damage", Oct. 17, 2011, Sensors and Actuators B: Chemical: International Journal Devoted to Research and Development of Physical and Chemical Transducers, Elsevier BV, NL, vol. 161, No. 1, pp. 334-340.

* cited by examiner

SENSOR ARRAY WITH ANTI-DIFFUSION REGION(S) TO EXTEND SHELF LIFE

This is a continuation application of U.S. Ser. No. 15/535,954, filed Jun. 14, 2017, now U.S. Pat. No. 9,978,633, issued May 22, 2018 which claims the benefit of U.S. National Stage of International Application No. PCT/US2015/066363, filed Dec. 17, 2015 and claims priority under 35 U.S.C. 119(e) to U.S. Provisional Application No. 62/094,478, filed Dec. 19, 2014. All of the applications are incorporated by reference herein in their entirety.

BACKGROUND

1. Field of the Disclosure

This disclosure relates to a sensor array with an extended shelf life.

2. Brief Description of the Related Art

Figure 1A:
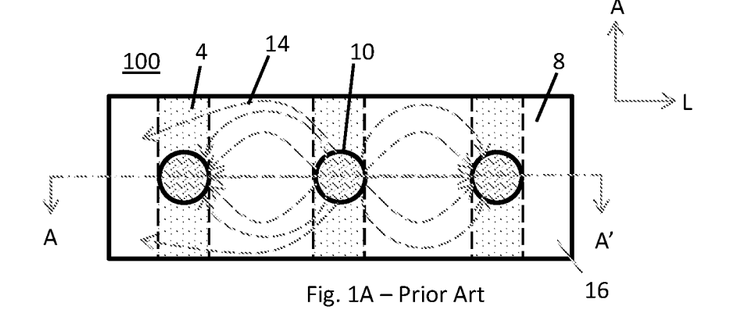
FIGS. 1A and 1B depict a top view and a side view along line A-A' of illustrative sensor array, respectively.
Figure 1B:
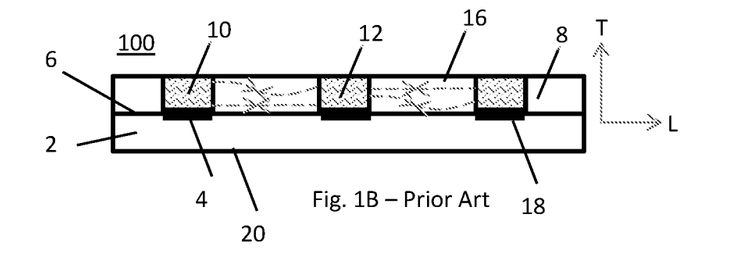

FIGS. 1A and 1B depicts a top and a side view along line A-A' of an illustrative sensor array 100 for testing a sample liquid for one or more analytes. Sensor array 100 includes at least one planar substrate 2, one or more planar conductors 4 disposed on a upper surface 6 of the substrate 2, at least one dielectric layer 8 disposed adjacent to the upper surface 6, and at least one well 10 created in dielectric layer 8. Each well 10 being associated with a planar conductor 4 and extending between an upper surface 16 of the dielectric layer 8 and an opposed lower surface 18 of the dielectric layer 8. The lower surface 18 being adjacent to the upper surface 6 of the substrate 2. Wells 10 may contain membrane chemistries 12 dispensed therein. When the sample liquid flows along the upper surface 16 of the dielectric layer 8, the membrane chemistries 12 may react with sample fluid. The reaction producing a response in the associated planar conductor 4.

SUMMARY OF THE INVENTIVE CONCEPT(S)

In one aspect, the inventive concepts disclosed herein are directed to a sensor array. The sensor array containing: (1) a first planar substrate, the first planar substrate having a first planar surface of the first planar substrate; (2) at least two coplanar electrodes disposed on the first planar surface of the first planar substrate; (3) a dielectric layer, the dielectric layer having opposed first and second planar surfaces, the second surface of the dielectric layer being proximate to and coplanar with the first surface of the first planar substrate, the dielectric layer being comprised of dielectric material; (4) a first reaction well and a second reaction well, the respective first and second reaction wells being a hole extending between the first surface of the dielectric layer and the first surface of the first planar substrate, the respective holes being positioned over a respective coplanar electrode and at least partially filled with at least one membrane chemistry, the membrane chemistry being in contact with the respective coplanar electrode; and (5) at least one anti-diffusion region, the anti-diffusion region extending between the first surface of the dielectric layer and the first surface of the first planar substrate, the anti-diffusion region being devoid of the dielectric material, the anti-diffusion region being at least partially disposed in between the first reaction well and the second reaction well, the anti-diffusion region blocking at least one diffusion path extending between the first reaction well and the second reaction well, the at least one diffusion path being a route along which diffusible elements of the membrane chemistry of at least one of the first reaction well or the second reaction well diffuse through the respective dielectric layer.

In another aspect of the inventive concepts, the length of the anti-diffusion region intersects a first imaginary straight line extending between the first reaction well and the second reaction well.

In yet another aspect of the inventive concept, the sensor array of claim 4, further comprising a third reaction well and the length of the anti-diffusion region intersects the first imaginary straight line and a second imaginary straight line extending between the centers of the second reaction well and the third reaction well.

DETAILED DESCRIPTION OF THE INVENTIVE CONCEPT(S)

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. The inventive concepts disclosed herein are capable of other embodiments or of being practiced or carried out in various ways. Also, it is to be understood that the phraseology and terminology employed herein is for the purpose of description and should not be regarded as limiting the inventive concepts disclosed and claimed herein in any way.

In the following detailed description of embodiments of the inventive concepts, numerous specific details are set forth in order to provide a more thorough understanding of the inventive concepts. However, it will be apparent to one of ordinary skill in the art that the inventive concepts within the instant disclosure may be practiced without these specific details. In other instances, well-known features have not been described in detail to avoid unnecessarily complicating the instant disclosure.

As used herein, the terms "comprises," "comprising," "includes," "including," "has," "having" or any other variation thereof, are intended to cover a non-exclusive inclusion. For example, a composition, a process, method, article, or apparatus that comprises a list of elements is not necessarily limited to only those elements but may include other elements not expressly listed or inherently present therein.

As used herein the terms "approximately," "about," "substantially" and variations thereof are intended to include not only the exact value qualified by the term, but to also include some slight deviations therefrom, such as deviations caused by measuring error, manufacturing tolerances, wear and tear on components or structures, settling or precipitation of cells or particles out of suspension or solution, chemical or biological degradation of solutions over time, stress exerted on structures, and combinations thereof, for example. As one example, "about" may refer a value that is ±10% of the stated value.

As used herein, the term "sample" and variations thereof is intended to include biological tissues, biological fluids, chemical fluids, chemical substances, suspensions, solutions (such as calibrating solutions or reference solutions), slurries, mixtures, agglomerations, tinctures, slides, powders, or other preparations of biological tissues or fluids, synthetic analogs to biological tissues or fluids, bacterial cells (prokaryotic or eukaryotic), viruses, single-celled organisms, lysed biological cells, fixed biological cells, fixed biological tissues, cell cultures, tissue cultures, genetically engineered cells and tissues, genetically engineered organisms, and combinations thereof, for example.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present). An inclusive or may be understood as being the equivalent to: at least one of condition A or B.

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

As used herein, any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Finally, the embodiments of the sensing device disclosed herein may be understood with reference to a first, second, and third direction such as, for example, lateral direction 'A', a longitudinal direction 'L' which is perpendicular to lateral direction 'A', and a transverse direction 'T' which is perpendicular to longitudinal direction 'L.' The longitudinal direction L and the lateral direction A extend horizontally as illustrated, and the transverse direction T extends vertically, though it should be appreciated that these directions may change depending, for instance, on the orientation of the sensor array. It should also be understood that first direction may be referred to as the lateral direction. It should also be understood that second direction may be referred to as the longitudinal direction. It should also be understood that third direction may be referred to as the transverse direction.

The inventive concepts disclosed herein are generally directed a sensor array device that has both a prolonged shelf life and use life but only requires only a minimal amount of sample volume in order to test two or more analytes concurrently. As should be understood by a person skilled in the art, 'shelf life' refers to the length of time the sensor array can be stored without becoming unfit for use while the related concept of 'use life' refers to the length of time during which the sensor can remain in use before becoming unfit for continued use. Depending on the sensor array, use life can concurrently or consecutively with shelf life.

Low sample volumes are desirable when the sample is limited, such as in the case of neonatal patients, or when the sample itself is expensive. As opposed to prior art configurations, which required the volume to increase with the number of analytes being detected, the required sample volume for the sensor arrays described herein can be greatly reduced by arranging individual sensors closely together along longitudinal direction L. However, referring back to the configuration described in connection with FIGS. 1B and 1A, some dielectric layers 8 are made of materials which allow for the diffusion of certain diffusible substances through the dielectric layer 8 (represented by diffusion paths 14). One example of such a diffusible substance are plasticizers located within certain membrane chemistries 12 contained, for example, within a well 10. As plasticizers emanate outwardly from membrane chemistries 12 in a particular well 10 along multiple diffusion paths 14 they form what can be referred to as a 'plasticizer front.' Each type of diffusible substance has its own characteristics which enable it to diffuse at a faster or slower rate than other diffusible substance through the same dielectric material. The rate at which diffusible substances diffuse through a dielectric is also, for example, a function of the (1) diffusible substance's size—small molecules diffusing faster than larger ones—(2) and the concentration of diffusible substances (higher concentrations of which can result in faster diffusion rates).

If certain diffusible substances from the membrane chemistry 12 of one well 10 diffuse into a second well 10 or come into contact with diffusible substances emanating from the second well 10, the resistance between the two wells 10 can become sufficiently low enough that an electrochemical connection is established between the first and second wells causing the two wells to no longer behave independently from one another. As a result, the diffusion of diffusible substances in membrane chemistries 12 directly impacts the shelf life of sensor array 100.

According to the inventive concepts discloses herein, in order to ensure the sensor array has a sufficiently long shelf life, anti-diffusion regions are positioned among the reaction wells 10 in order to slow, or stop, the processes of diffusion. The use of anti-diffusion regions, as described herein, can be used to optimize the number of sensors that can be fit into a sensor array designed for reduced sample liquid volumes (e.g., less than 100 µL) while extending the sensor array's shelf life. Embodiments of sensor arrays with illustrative anti-diffusion regions are discussed in connection with FIGS. 2A through 6B below.

FIGS. 1A and 1B depict, respectively, a top view and a side view along line A-A' of illustrative sensor array 100. Sensor array 100 includes a planar substrate 2. Planar substrate 2 may be substantially planar with a substantially planar upper surface 6 and substantially planar lower surface 20 of the planar substrate 2. The upper surface 6 and lower surface 20 both extend in the lateral direction A and the longitudinal direction L and are separated by a thickness extending along the transverse direction T. Planar substrate 2 may be formed using a variety of methods and materials known to a person of ordinary skill in the art. For example, planar substrate may be constructed using one or more of, for example, flex PCB, PET, PI, etc.

Sensor array 100 further includes one or more planar conductors 4 disposed on—and coplanar with—upper surface 6 of the substrate 2 (three examples of conductors 4 are depicted in FIGS. 1A and 1B), a planar dielectric layer 8 disposed adjacent to as well as coplanar with the upper surface 6, and a plurality of wells 10 created in dielectric layer 8. Wells 10 extend along transverse direction T between planar upper surface 16 and planar lower surface 18 of dielectric layer 8.

While not shown in FIG. 1A or 1B, the assay device 100 may also contain additional layers disposed above the dielectric layer 8 and opposite substrate 2. These additional layers may define a fluid flow path that is at least partially above one or more, up to all, of wells 10 and facilitates the flow of the liquid sample towards the one or more wells 10. Alternatively, a structure external to assay device 100 may form the flow path.

Coplanar conductors 4 may be formed using a variety of methods and materials known to a person of ordinary skill in the art. For example, coplanar conductors 4 may be formed using a thick film approach (e.g., screen printing, rotogravure, pad printing, stenciling conductive material such as carbon, Cu, Pt, Pd, Au, and/or Nanotubes, etc. . . . ) or a thin film approach (e.g., by sputtering, thermal spraying, and/or cold spraying conductive material). Coplanar conductors 4 may be partitioned using, for example, laser ablation. It should be understood that the configuration of conductors 4 in the Figures described here are merely for illustrative purposes only and a person of ordinary skill in the art will appreciate that conductors 4 may be distributed on substrate 2 in a variety of alternative ways. While not shown in the Figures, one or more, up to all, of the conductors 4 are electrically coupled to a contact region elsewhere on the sensor assembly. These electrical contacts enable the sensor assembly to be electrically connected to a processor and/or an external device.

The dielectric layer 8 may be comprised of one or more individual layers that are collectively referred to as the dielectric layer 8. The one or more planar dielectric layers 8 are disposed adjacent to the upper surface 6 of the planar substrate 2. The dielectric layer(s) 8 may be formed using a variety of methods and materials known to a person of ordinary skill in the art. For example, dielectric layers 8 may be made by laminating a dielectric onto the planar substrate using an adhesive layer (or another means of adhesion) disposed in between the dielectric layer 8 and the substrate 2. Alternatively, dielectric layer(s) could itself be a pressure sensitive adhesive layer or can be integrated into planar substrate 2 by forming dielectric layer(s) 8 directly on top of upper surface 6 and coplanar conductors 4.

Wells 10 are holes (also referred to as apertures) in the dielectric layer 8 and extend along the transverse direction T between an upper surface 16 of the dielectric layer 8 and the upper surface 6 of the substrate 2. If an adhesive layer is present, wells 10 may also extend through the adhesive layer disposed in between the dielectric layer 8 and the substrate 2. The cross section of respective wells 10 extend along the lateral direction A and the longitudinal direction L. The cross section of respective wells 10 may be circular, ovular, or any other regular or irregular shape. Individual wells 10 may be positioned over respective conductors 4 either (1) directly above respective conductors 4 and aligned along transverse direction T—as depicted in the Figures—or (2) above respective conductors 4 along transverse direction T and offset along one or both of lateral direction 'A' and longitudinal direction 'L.' In this offset configuration a hydrophilic layer (not shown) may be positioned between an individual well 10 and the respective conductor 4 along transverse direction T to aid in signal transduction between the respective conductor 4 and the membrane chemistry 12 disposed inside the well 10. Wells 10 may contain membrane chemistries 12 dispensed therein such that the membrane chemistries 12 contact the respective conductors 4 underneath. While the wells 10 in FIGS. 1A and 1B are depicted as being centered around, and evenly spaced along, line A-A' it should be understood that they can be arranged in a variety of alternative configurations. When the sample liquid flows along the upper surface 16 of the dielectric layer 8, the membrane chemistries 12 may react with sample fluid. The reaction producing a response in the associated planar conductor 4. The combination of a well 10, membrane chemistries 12 contained therein, as well as the associated conductor 4 may be collectively referred to as a sensor.

As discussed above, some dielectric layers 8 are made of materials which may allow diffusible elements to diffuse there through. For example, certain membrane chemistries 12 may contain such diffusible elements which diffuse outwardly from their respective wells 10 through dielectric layer 8. A membrane chemistry 12 containing diffusible elements capable of diffusing through a given dielectric layer 8 may be understood to as being "compatible" with the dielectric layer 8. When membrane chemistry 12 do not contain diffusible elements capable of diffusing through the dielectric layer 8, the membrane chemistry 12 may be understood as not being compatible with the dielectric layer 8. An example of a diffusible element is a plasticizer. It should be understood that sensor array 100 may contain a variety of different types of membrane chemistries 12—one or more of which may be compatible with the dielectric layer 8 and one or more of which may not be compatible with the dielectric layer 8. It should be further appreciated that dielectric layer 8 may be made from a variety of materials known to a person of ordinary skill—each of which have certain membrane chemistries 12 that are or are not compatible therewith.

When a membrane chemistry 12 contains diffusible elements in a respective well 10 that are compatible with the respective dielectric layer 8, diffusible elements of certain membrane chemistries 12 diffuse through the dielectric layer 8 outwardly from the well 10 along routes referred to as diffusion paths 14. As depicted in FIGS. 1A-1B, illustrative diffusion paths 14 may extend through the dielectric layer 8 along one, two, or all three of the lateral direction A, the longitudinal direction L, and the transverse direction T. For example, diffusion paths 14 may, for example but not limited to, take one or more of a random path, a straight line, an arc, a zig-zag route, or serpentine route through dielectric layer 8. Consequently, diffusion paths 14 may have a variety of lengths. Using well 10A as an example, when diffusion paths 14 extending from well 10A either (1) reaches second well 10B (as shown in FIG. 1A) or (2) intersects a diffusion path 14 extending from the second well 10B (as shown in FIG. 1B), the plasticizers from the respective membrane chemistries 12 of wells 10A and 10B diffuse together—resulting in an electrochemical connection in which the resistance between the pair of wells 10A and 10B becoming sufficiently low enough that wells 10A and 10B no longer behave independently from one another.

Figure 2A:
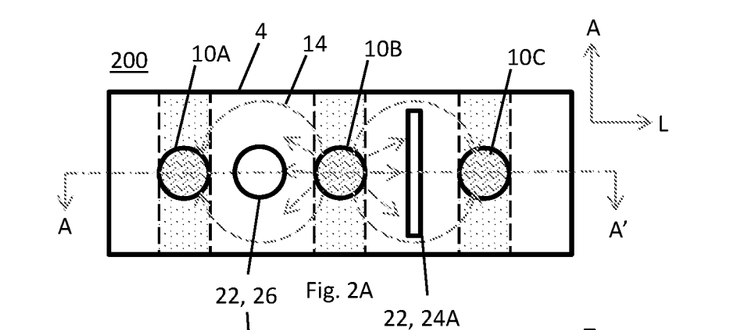
FIGS. 2A and 2B depict a top view and a side view along line A-A' of illustrative sensor array, respectively.
Figure 2B:
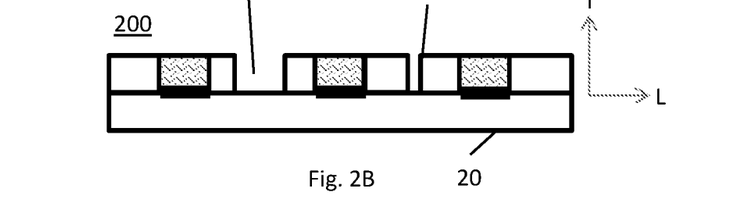

Turning now to FIGS. 2A and 2B, which depict a top view and a side view along line A-A' of illustrative sensor array 200—which resembles sensor array 100 in certain respects. In order to extend the shelf life of a sensor array, one or more anti-diffusion regions 22 may be located within the dielectric layer 8 in order to slow the processes of diffusion of one or more of membrane chemistries 12. An anti-diffusion region 22 is a region that prevents the diffusion of the diffusible elements of the membrane chemistry 12 there through. The anti-diffusion region 22 is located between the upper surface 16 of the dielectric layer 8 and the upper surface 6 of the planar substrate 2. If an adhesive layer is located in between the dielectric layer 8 and the substrate layer 2, the anti-diffusion region may or may not extend through the adhesive layer as well—depending on whether the diffusible elements are capable of diffusing through the adhesive layer too. Each anti-diffusion region 22 is positioned in between two wells 10 in order to block one or more diffusion paths 14 between two reaction wells 10. For example, each anti-diffusion region 22 can be positioned in order to block at least the most direct diffusion path(s) 14 between two wells. The most direct diffusion path(s) 14 between any two wells may be understood as being the shortest route(s) the diffusion elements can take through the dielectric layer 8 between those two wells.

As should be appreciated to a person of ordinary skill in the art, anti-diffusion regions 22 can be formed in a variety of ways. For example, anti-diffusion regions 22 can be formed in the dielectric layer(s) and (if applicable) the adhesive layer using one or more of: laser ablation, cutting, scoring, stamping, and grinding.

As shown and described in the Figures, the anti-diffusion region 22 may be a region in the dielectric layer 8 that is devoid of any materials (e.g., an air gap) with a height that extends between the upper surface of the substrate 2 and the upper surface 16 of the dielectric layer 8 along the transverse direction T. Alternatively, the above described air gap may be partially or completely covered along its length using a cover material adjacent to surface 6 that blocks diffusion paths 14 as well as the sample liquid from flowing into the anti-diffusion region 22. In yet another example, anti-diffusion regions 22 may anti-diffusion regions 22 may be filled with a blocking material which blocks diffusion paths 14 in dielectric layer 8 from continuing through the anti-diffusion region—such as a material that is not compatible with one or more of the diffusible elements in one or more of membrane chemistries 12 of sensor array 200. If an adhesive layer is located in between the dielectric layer 8 and the substrate layer 2, the height of the anti-diffusion region 22 may or may not extend through the adhesive layer as well. For example, when the adhesive layer is compatible with any of the membrane chemistries 12, the height of the anti-diffusion region 22 can extend through the adhesive layer. Anti-diffusion regions 22 also have a length that extends along one or both of the lateral direction A and the longitudinal direction L, and a width that extends along one or both of the lateral direction A and the longitudinal direction L. As should be understood by a person skilled in the art, each of the anti-diffusion regions 22 discussed above can be utilized separately or in combination in the configurations explained below.

In certain embodiments, an anti-diffusion region 22 may be circular. For example, a circular anti-diffusion region 22 may have the size and space of a well 10 but are devoid of membrane chemistry 12. These circular anti-diffusion regions 22 can be placed in between two wells 10 which each contain chemistry 12. While easy to manufacture, circular anti-diffusion regions 22 are not space efficient since they take up a significant amount of surface area.

In contrast to a circular anti-diffusion region 22, a trench 24 configuration is more space efficient. Illustrative embodiments of trench 24 have a rectangular profile (when viewed along, for example, the lateral direction A and the longitudinal direction L) with a length and a width. The length of respective trenches 24 may be linear (extending, for example, along a straight path along the lateral direction A) or non-linear (extending, for example, along a curved path along both of the lateral direction A and longitudinal direction L). Trenches may have a uniform width (extending, for example, along the longitudinal direction L) or a variable width. While the length and the width of exemplary trenches 24 may be substantially equal, the length is typically longer than the width. In certain embodiments, trenches 24 may have a width that is as narrow as possible. The narrowest possible width of a trench 24 depends, in part, on the type of material which comprises the dielectric layer. Certain dielectric materials are "soft" enough for too narrow of a trench 24 too reseal itself—thus the width of the trench 24 should be wide enough to prevent resealing during a sensor assemblies predetermined shelf life. The narrowest possible width of a trench 24 also depends, in part, on the method used to form the trench 24. For example, if the trench is formed with a laser, the laser may scorch the side walls of the trench 24—thereby helping to avoid the trench from resealing. Depending on the dielectric material used, exemplary trench widths include: 1 um, 2 um, 10 um, 100 um, mm, 0.75 mm, 0.5 mm, and 0.25 mm. The narrowest possible width of a trench 24 further depends on whether the trench is devoid of material. If a trench is filled with a material it need only be narrow enough to contain the material. Depending on the width of the trench 24, the type of dielectric material used in the dielectric layer 8, and the technique used to make the trench 24, the width of the trench may vary significantly along its length. For Example, if a 1 um trench 24 is created by scoring, the width of the trench could vary by as much as 100% (±1 um) or more.

It should be understood that while the trenches 24 typically have a uniform width along the trench height (along the transverse direction T), this need not be the case. Exemplary trenches may have a 'V' shape (where the width of the trench 24 is widest at the upper surface 16 of the dielectric layer 8). Depending on the type of dielectric material used, such a 'V' shaped trench may prevent the trench from resealing or facilitate the insertion of material into the trench 24.

In order to improve shelf life, the trench 24 is positioned in order to block, at least, the diffusion path(s) traveling along the shortest route(s) (within the dielectric layer 8 or adhesive layer) between two wells 10. When two wells 10 are adjacent to one another, the trench 24 is positioned such that it intersects, at least, the shortest imaginary straight line extending between the two wells 10.

FIGS. 2A and 2B depict an illustrative configuration of a sensor assembly 200 with a linear trench 24A shaped anti-diffusion regions 22 and a circular shaped anti-diffusion region 26. As with trenches 24, circular shaped anti-diffusion region 26 may or may not have a uniform width along its height (along the transverse direction T). FIG. 2A is a top view of the sensor and FIG. 2B is a view along line A-A'. FIGS. 2A and 2B depict wells 10A, 10B, and 10C centered around, and evenly spaced along, line A-A'. Trench 24A in FIGS. 2A and 2B is positioned between wells 10B and 10B, 10C, respectively, and oriented such that its respective length is perpendicular to and centered around line A-A'. By positioning at least part of anti-diffusion regions 22 (e.g., trench 24A and circular region 26) in between each pair of wells 10A, 10B and 10B, 10C, the trenches 24A block at least one diffusion path extending between the each pair of reaction wells 10A, 10B and 10B, 10C. In particular, trench 24A and circular region 26 in FIGS. 2A and 2B block not only the shortest diffusion path between each pair of wells 10A, 10B and 10B, 10C, but many others. As shown in FIG. 2A, a significant number of diffusion paths are blocked by the trench 24A and circular region 26. In order to circumvent one of the trenches 24A, a diffusion path must be significantly longer than the shortest diffusion path there by prolonging shelf life.

Figure 3A:
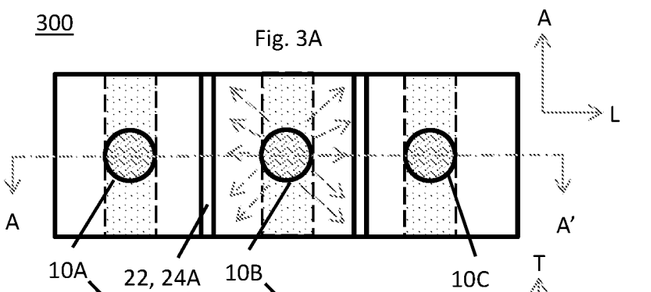
FIGS. 3A and 3B depict a top view and a side view along line A-A' of illustrative sensor array, respectively.
Figure 3B:
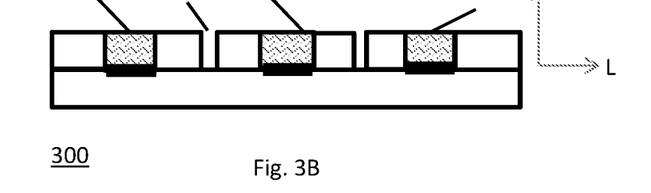

In FIGS. 2A and 2B, the length of trench 24A does not extend through the entire length of the dielectric layer 8 along the lateral direction A. By not extending the trench 24A the entire length of the dielectric layer 8, the dielectric layer 8 can continue to provide structural rigidity to the sensor assembly 200 in those embodiments where the dielectric layer 8 is needed to maintain the structural integrity of the sensor assembly 200 (such as when planar substrate 2 is insufficiently rigid or when the sensor assembly 200 is not otherwise structurally supported). However, as shown in FIGS. 3A and 3B, when the dielectric layer 8 is not needed to maintain structural integrity, trenches 24A may extend through the entire length of the dielectric layer 8. By extending the entire length of the dielectric layer 8, the trenches 24A in FIGS. 3A and 3B bifurcate the dielectric layer into multiple isolated regions, thereby blocking all potential diffusion paths 14. FIGS. 3A and 3B depict a top view and a side view along line A-A' of illustrative sensor array 300—which resembles sensor array 200 in certain respects.

While the trenches 24A can have many different lengths, the longer the length of any given trench 24A, the more diffusion paths 14 it will block. Thus, in an illustrative embodiment, the length of individual trenches 24A is equal to the diameter of an adjacent well 10. In other embodiments, the length of individual trenches 24A is one of about 1.2, 1.5, 1.7, 2, 2.2, 2.5, 2.7, 3, 3.2, 3.5, 3.7, 4, 4.2, 4.5, 4.7, or 5 times the diameter of an adjacent well.

While trenches 24A in FIGS. 2A, 2B, 3A, and 3B are depicted as being symmetrically positioned in between pairs of wells 10, it should be understood that the lengths of trenches 24A need not be centered along line A-A' nor must they extend perpendicularly to line A-A'. Additionally, the trenches 24A do not need to be centered in between adjacent wells.

Figures 4A, 4B:
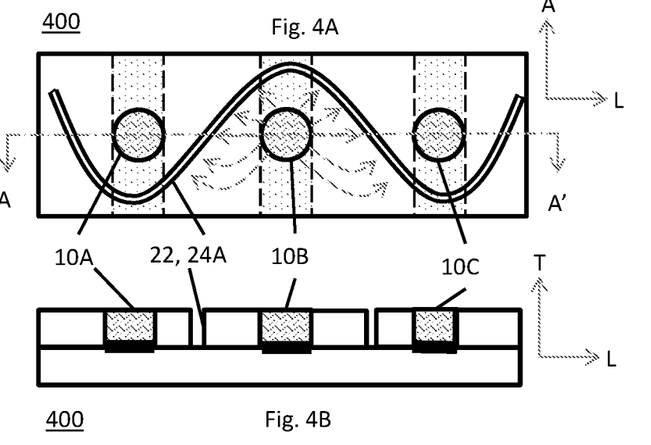
FIGS. 4A and 4B depict a top view and a side view along line A-A' of illustrative sensor array, respectively.

FIGS. 4A and 4B depict an illustrative configuration of a sensor assembly 400, which resembles sensor array 200 in certain respects, with a single, nonlinear trench 24B shaped anti-diffusion regions 22. FIG. 4A is a top view of the sensor and FIG. 4B is a view along line A-A'. FIGS. 4A and 4B depict wells 10A, 10B, and 10C centered around, and evenly spaced along, line A-A'. Nonlinear trench 24B in FIGS. 4A and 5B extends through the gap between wells 10A and 10B (thereby blocking all of the diffusion paths between wells 10A and 10B), around well 10B, and then through the gap between wells 10B and 10C (thereby blocking all of the diffusion paths between wells 10B and 10C). Stated differently, nonlinear trench 24B takes a serpentine shaped path which intersects both (1) an imaginary straight line between wells 10A and 10B and (2) an imaginary straight line between wells 10B and 10C. It should be further appreciated that the nonlinear trench can be extended to intersect imaginary straight lines between additional pairs of wells 10 and is not limited to an embodiment of a sensor assembly having three wells 10.

While the trench 24B in FIGS. 4A and 4B resembles a sine wave which oscillates about line A-A' in between the wells 10A, 10B, and 10C, a single nonlinear trench 24B can be virtually any shape. For example, a nonlinear trench 24B can resemble periodic or non-periodic waveforms—such as, but not limited to, a square wave, triangle wave, saw tooth wave. Thus a single nonlinear trench 24B can extend between multiple pairs of wells to obstruct multiple diffusion paths 14.

Figures 5A, 5B:
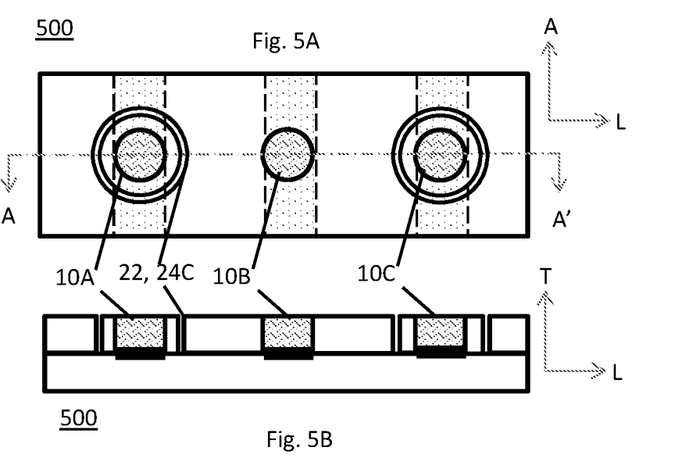
FIGS. 5A and 5B depict a top view and a side view along line A-A' of illustrative sensor array, respectively.

FIGS. 5A and 5B depict a top view and a side view along line A-A' of illustrative sensor array 300—which resembles sensor array 200 in certain respects, with multiple nonlinear trench 24C shaped anti-diffusion regions 22. FIG. 5A is a top view of the sensor and FIG. 5B is a view along line A-A'. FIGS. 5A and 5B depict wells 10A, 10B, and 10C centered around, and evenly spaced along, line A-A'. Nonlinear trenches 24C in FIGS. 5A and 5B completely surround respective wells 10 (thereby blocking all of the diffusion paths between, for example, wells 10A and 10B). While trenches 24C are depicted as being circular, it should be appreciated that they can be any regular shape (such as a triangle, an oval, or an octagon) or any irregular shape. It should also be appreciated that not every well 10 needs to be surrounded by a trench 24C. For example, in FIG. 5A, well 10B does not need to be surrounded by a trench because both wells 10A and 10C are surrounded, thus preventing any diffusion paths from escaping.

Figures 6A, 6B:
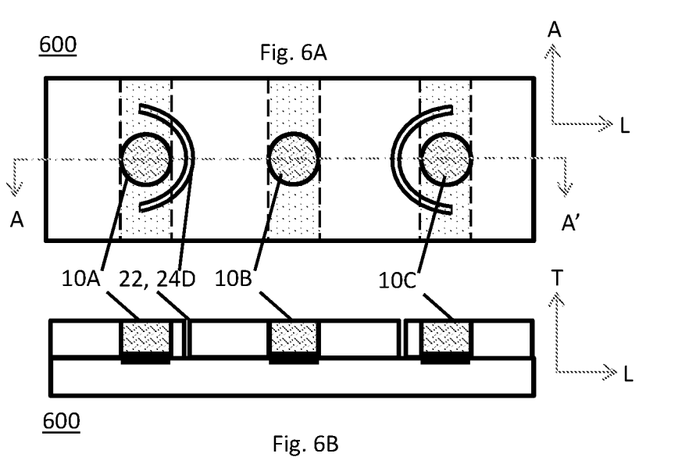
FIGS. 6A and 6B depict a top view and a side view along line A-A' of illustrative sensor array, respectively.

FIGS. 6A and 6B depict a top view and a side view along line A-A' of illustrative sensor array 600—which resembles sensor array 200 in certain respects, with multiple nonlinear trench 24D shaped anti-diffusion regions 22. FIG. 6A is a top view of the sensor and FIG. 6B is a view along line A-A'. FIGS. 6A and 6B depict wells 10A, 10B, and 10C centered around, and evenly spaced along, line A-A'. Nonlinear trenches 24D in FIGS. 6A and 6B partially surround respective wells 10 (thereby blocking a large number of diffusion paths from extending towards other). While trenches 24D are depicted as being curved, it should be appreciated that they can be any regular shape or any irregular shape. It should also be appreciated that not every well 10 needs to be surrounded by a trench 24D. For example, in FIG. 6A, well 10B does not need to be surrounded by a trench because both wells 10A and 10C are partially surrounded by a trench 24D which prevents a significant number diffusion paths from either well 10A or well 10C from reaching well 10B.

What is claimed is:

1. A sensor array comprising:
    a first planar substrate, the first planar substrate having a first planar surface of the first planar substrate;
    at least two coplanar electrodes disposed on the first planar surface of the first planar substrate;
    a dielectric layer, the dielectric layer having opposed first and second planar surfaces, the second surface of the dielectric layer being proximate to and coplanar with the first surface of the first planar substrate, the dielectric layer being comprised of dielectric material;
    a first reaction well and a second reaction well, the respective first and second reaction wells being a hole extending between the first surface of the dielectric layer and the first surface of the first planar substrate, the respective holes being positioned over a respective coplanar electrode and at least partially filled with at least one membrane chemistry, the membrane chemistry being in contact with the respective coplanar electrode; and
    at least one anti-diffusion region, the anti-diffusion region extending between the first surface of the dielectric layer and the first surface of the first planar substrate, the anti-diffusion region being devoid of the dielectric material, the anti-diffusion region being at least partially disposed in between the first reaction well and the second reaction well, the anti-diffusion region blocking at least one diffusion path extending between the first reaction well and the second reaction well, the at least one diffusion path being a route along which diffusible elements of the membrane chemistry of at least one of the first reaction well or the second reaction well diffuse through the respective dielectric layer,
    wherein the anti-diffusion region extends along a length, the length extending along at least a first direction, the first direction being perpendicular to a second direction, the second direction extending between the first and second surfaces of the dielectric layer, wherein the anti-diffusion region extends along the entire length of the dielectric layer.

2. The sensor array of claim 1, wherein the anti-diffusion region contains a blocking material between the first surface of the dielectric layer and the first surface of the first planar substrate, the blocking material blocking the at least one diffusion path.

3. The sensor array of claim 1, wherein the anti-diffusion region contains a cover adjacent to the first surface of the dielectric layer, the cover blocking the at least one diffusion path.

4. The sensor array of claim 1, wherein anti-diffusion region further extends along a third direction, the third direction being perpendicular to both the first direction and the second direction.

5. The sensor array of claim 1, further comprising an adhesive layer disposed in between the first surface of the first planar substrate and the second surface of the dielectric layer.

6. A method of making the test strip as described in claim 1.

7. The sensor array of claim 1, wherein the length of the anti-diffusion region intersects a first imaginary straight line extending between the first reaction well and the second reaction well.

8. The sensor array of claim 7, further comprising a third reaction well; and wherein the length of the anti-diffusion region intersects the first imaginary straight line and a second imaginary straight line extending between the centers of the second reaction well and the third reaction well.

9. The sensor array of claim 8, wherein the first imaginary line is parallel to the second imaginary line.

10. A sensor array comprising:
a first planar substrate, the first planar substrate having a first planar surface of the first planar substrate;
at least two coplanar electrodes disposed on the first planar surface of the first planar substrate;
a dielectric layer, the dielectric layer having opposed first and second planar surfaces, the second surface of the dielectric layer being proximate to and coplanar with the first surface of the first planar substrate, the dielectric layer being comprised of dielectric material;
a first reaction well and a second reaction well, the respective first and second reaction wells being a hole extending between the first surface of the dielectric layer and the first surface of the first planar substrate, the respective holes being positioned over a respective coplanar electrode and at least partially filled with at least one membrane chemistry, the membrane chemistry being in contact with the respective coplanar electrode; and at least one anti-diffusion region, the anti-diffusion region extending between the first surface of the dielectric layer and the first surface of the first planar substrate, the anti-diffusion region being devoid of the dielectric material, the anti-diffusion region being at least partially disposed in between the first reaction well and the second reaction well, the anti-diffusion region blocking at least one diffusion path extending between the first reaction well and the second reaction well, the at least one diffusion path being a route along which diffusible elements of the membrane chemistry of at least one of the first reaction well or the second reaction well diffuse through the respective dielectric layer, wherein the anti-diffusion region extends along a length, the length extending along at least a first direction, the first direction being perpendicular to a second direction, the second direction extending between the first and second surfaces of the dielectric layer, wherein the anti-diffusion region extends along less than the entire length of the dielectric layer.

11. The sensor array of claim 10, wherein the anti-diffusion region contains a blocking material between the first surface of the dielectric layer and the first surface of the first planar substrate, the blocking material blocking the at least one diffusion path.

12. The sensor array of claim 10, wherein anti-diffusion region further extends along a third direction, the third direction being perpendicular to both the first direction and the second direction.

13. The sensor array of claim 10, further comprising an adhesive layer disposed in between the first surface of the first planar substrate and the second surface of the dielectric layer.

14. The sensor array of claim 10, wherein the anti-diffusion region contains a cover adjacent to the first surface of the dielectric layer, the cover blocking the at least one diffusion path.

15. A method of making the test strip as described in claim 10.

16. The sensor array of claim 10, wherein the length of the anti-diffusion region intersects a first imaginary straight line extending between the first reaction well and the second reaction well.

17. The sensor array of claim 16, further comprising a third reaction well; and wherein the length of the anti-diffusion region intersects the first imaginary straight line and a second imaginary straight line extending between the centers of the second reaction well and the third reaction well.

18. The sensor array of claim 17, wherein the first imaginary line is parallel to the second imaginary line.

* * * * *